US009339406B2

(12) United States Patent
Burke et al.

(10) Patent No.: US 9,339,406 B2
(45) Date of Patent: May 17, 2016

(54) LOWER SPINE BRACE

(71) Applicants: Steven R. Burke, Huntington Beach, CA (US); Geoffrey Garth, Long Beach, CA (US); Jozsef Horvath, Fullerton, CA (US)

(72) Inventors: Steven R. Burke, Huntington Beach, CA (US); Geoffrey Garth, Long Beach, CA (US); Jozsef Horvath, Fullerton, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 464 days.

(21) Appl. No.: 13/763,188

(22) Filed: Feb. 8, 2013

(65) Prior Publication Data

US 2014/0228727 A1    Aug. 14, 2014

(51) Int. Cl.
*A61F 5/00* (2006.01)
*A61F 5/02* (2006.01)
*A61F 5/01* (2006.01)

(52) U.S. Cl.
CPC .. *A61F 5/028* (2013.01); *A61F 5/01* (2013.01)

(58) Field of Classification Search
CPC ............. A45F 3/02; A45F 3/005; A45F 5/10; A45F 2003/025; A45F 2003/146; A45F 2005/1013; A45F 2005/1033; A45F 2005/108; A45F 3/04; A45F 3/14; A45F 5/1046; A45F 2003/001; A45F 2003/003
USPC ........................................ 24/612; 602/16–28
See application file for complete search history.

(56) References Cited

U.S. PATENT DOCUMENTS

| | | |
|---|---|---|
| 4,080,962 A | 3/1978 | Berkeley |
| 5,179,942 A | 1/1993 | Drulias |
| 5,188,586 A | 2/1993 | Castel |
| 5,346,461 A | 9/1994 | Heinz |
| 5,433,697 A | 7/1995 | Cox |
| 5,437,617 A | 8/1995 | Heinz |
| 5,484,395 A | 1/1996 | DeRoche |
| 5,690,609 A | 11/1997 | Heinze, III |
| RE35,940 E | 10/1998 | Heinz |
| 6,099,490 A | 8/2000 | Turtzo |
| 6,102,879 A | 8/2000 | Christensen |
| 6,190,343 B1 | 2/2001 | Heinz |
| 6,213,968 B1 | 4/2001 | Heinz |
| 6,322,529 B1 | 11/2001 | Chung |
| 6,503,215 B1 | 1/2003 | Reinhardt |
| 6,517,502 B2 | 2/2003 | Heyman |
| 6,602,214 B2 | 8/2003 | Heinz |
| 6,676,620 B2 | 1/2004 | Schwenn |
| 6,964,644 B1 | 11/2005 | Garth |
| 7,001,348 B2 | 2/2006 | Garth |
| 7,186,229 B2 | 3/2007 | Schwenn |
| 8,142,377 B2 | 3/2012 | Garth |

(Continued)

FOREIGN PATENT DOCUMENTS

FR      2682869 A1    4/1993

*Primary Examiner* — Michael Brown
(74) *Attorney, Agent, or Firm* — Fish & Tsang LLP

(57) ABSTRACT

A brace comprises one or more panels having an aperture or slit that is at least partially defined by a first portion and a second portion. Each panel can couple with a lateral support that is configured to wrap around a portion of a wearer's body. One or both of the first and second portions can comprise an arc that is configured to prevent a twisting of the panel when the brace is tightened around a wearer. One or both of the first and second portions can additionally or alternatively comprise a plurality of protrusions configured to interact with a portion of a lateral support to thereby assist in maintaining a vertical position of the lateral support with respect to the panel.

19 Claims, 6 Drawing Sheets

(56) References Cited

U.S. PATENT DOCUMENTS

| | | |
|---|---|---|
| 8,235,925 B2 | 8/2012 | Cavalieri et al. |
| 2001/0020144 A1 | 9/2001 | Heinz |
| 2001/0034498 A1 | 10/2001 | Heyman |
| 2005/0092789 A1* | 5/2005 | Giacona .................... 224/148.6 |
| 2005/0251074 A1 | 11/2005 | Latham |
| 2005/0267390 A1 | 12/2005 | Garth |
| 2005/0273025 A1 | 12/2005 | Houser |
| 2006/0004313 A1 | 1/2006 | Heinz |
| 2009/0082707 A1 | 3/2009 | Rumsey |
| 2009/0192425 A1 | 7/2009 | Garth |
| 2009/0204042 A1 | 8/2009 | Park |
| 2010/0217167 A1 | 8/2010 | Ingimundarson |
| 2011/0144551 A1* | 6/2011 | Johnson .................... A61F 5/30 602/19 |
| 2011/0213284 A1 | 9/2011 | Garth et al. |
| 2011/0295169 A1 | 12/2011 | Hendricks |
| 2012/0022419 A1 | 1/2012 | Ingimundarson |
| 2012/0245502 A1 | 9/2012 | Garth |
| 2012/0253251 A1 | 10/2012 | Thornton |
| 2013/0092139 A1* | 4/2013 | Summers et al. ................ 124/31 |

\* cited by examiner

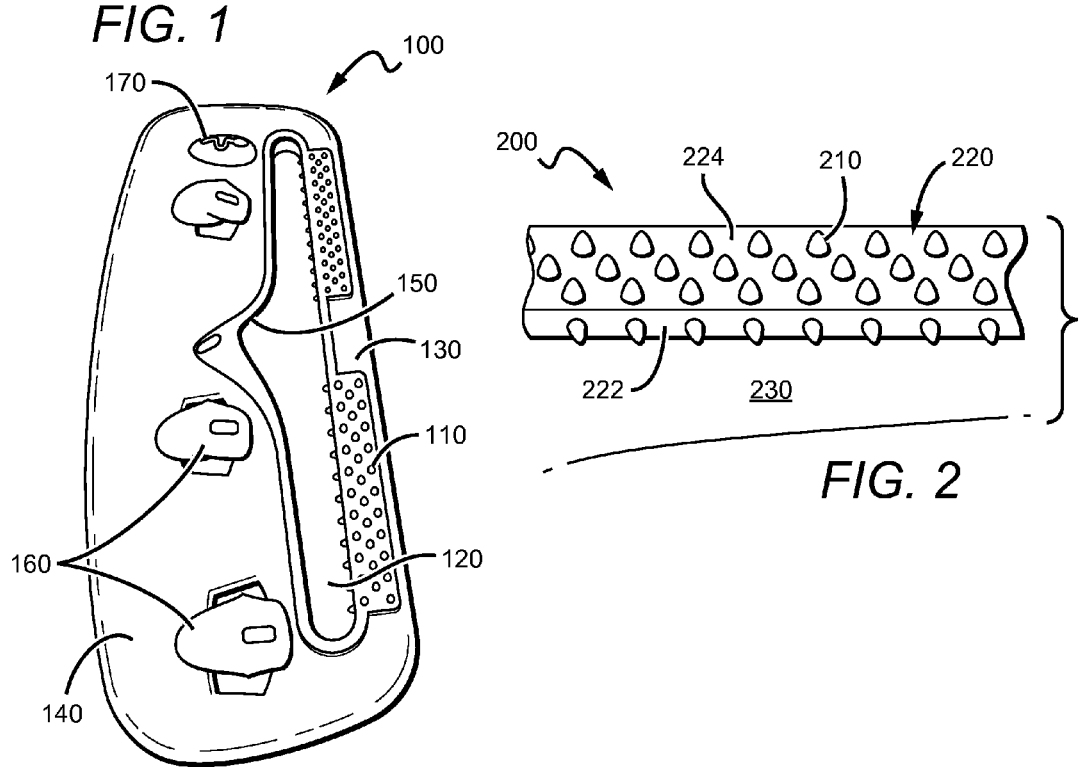
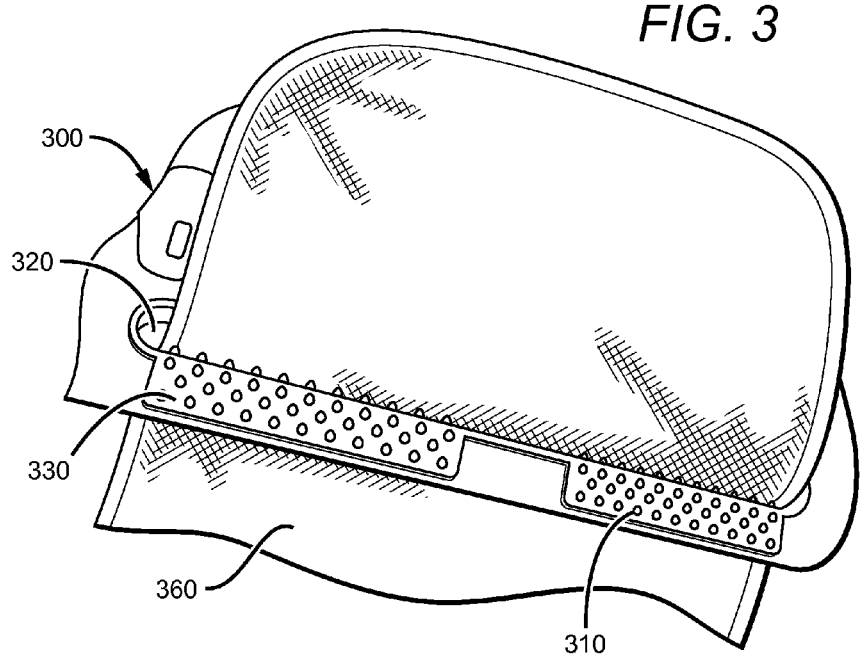

FIG. 6A
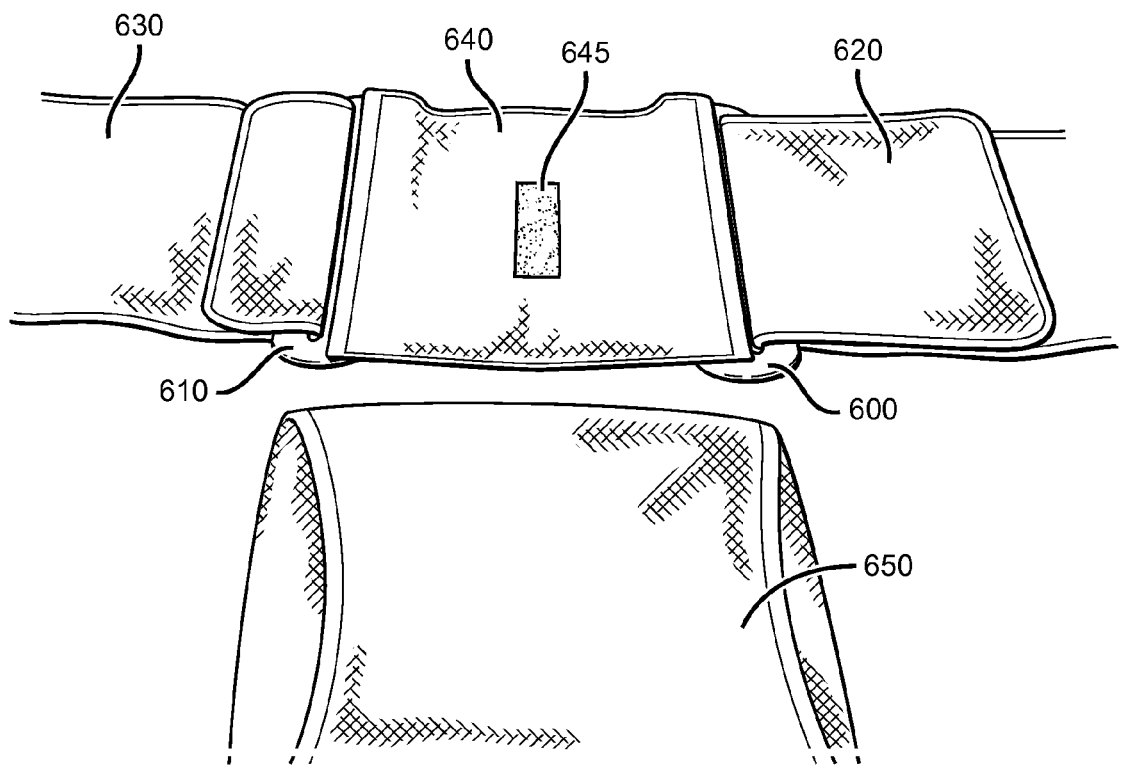
FIG. 6B
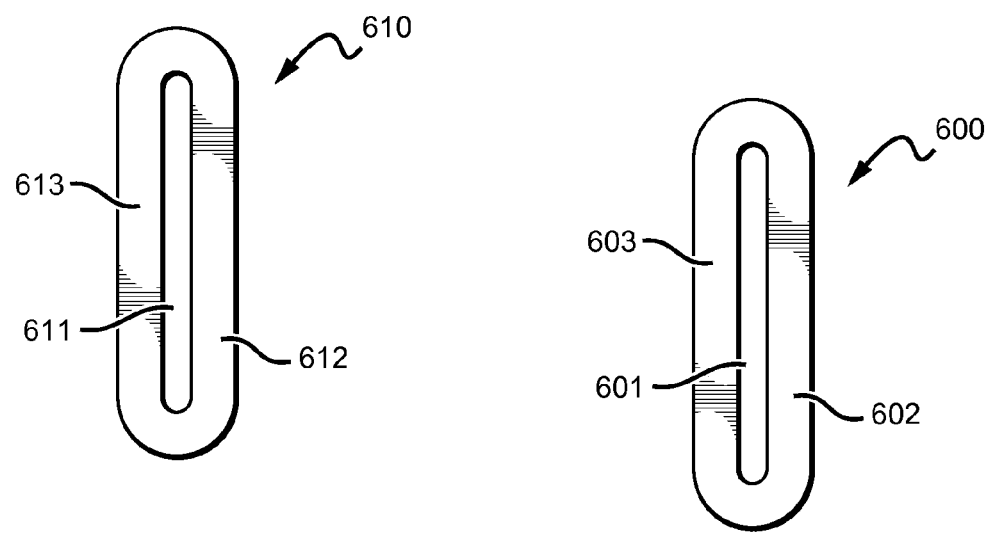
FIG. 6C

LOWER SPINE BRACE

FIELD OF THE INVENTION

The field of the invention is orthotics.

BACKGROUND

The following background discussion includes information that may be useful in understanding the present invention. It is not an admission that any of the information provided herein is prior art or relevant to the presently claimed invention, or that any publication specifically or implicitly referenced is prior art.

Orthotic devices are provided for partial or substantial immobilization of the torso to stabilize the back. These orthotic devices are back braces which can be fitted snugly around the torso of a wearer. Such back braces are effective in achieving spinal stability if worn properly. For many users, back braces are difficult to appropriately position and fasten. Without being consistently worn and properly adjusted, the effectiveness is substantially reduced.

US Patent Application Publication No. 2011/0213284 and U.S. Pat. No. 7,001,348 to Garth et al. overcome some of the problems discussed above. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

It has yet to be appreciated that a brace's adjustability can be maintained without reducing comfort to a wearer. Thus, there is still a need for improved adjustable braces.

SUMMARY OF THE INVENTION

The inventive subject matter provides apparatus, systems and methods in which one could use a brace to support a body of a wearer. Preferred braces are configured to provide support to a lower spine or other area of a wearer, and comprises one or more panels having an aperture sized and dimensioned to receive an end portion of a lateral support (e.g., belt).

In one aspect of the inventive subject matter, the aperture of the panel can be at least partially defined by a first wall and a second wall. One or both of the walls can be arced to prevent a twisting or other deformation of the panel. It is especially preferred that the first wall is substantially flat along a bottom surface, while the second wall's bottom surface has an arced portion. As used herein, the term "substantially flat" includes completely flat surfaces as well as those surfaces having a curve of no more than 5 degrees from horizontal.

Including an arced portion in the panel advantageously allows the first wall to maintain substantially flat, while the second wall including the arced portion can flex inwardly toward a wearer. In contrasts, panels without an arced portion such as those found in the prior art would have the first wall or portion flex outwardly while the second wall or portion flexes inwardly when pressure is applied to the panel via a lateral panel or otherwise.

It is contemplated that an arced portion can comprise any suitable shape comprising a visible curvature. One exemplary arc shape comprises a hollow substantially half-dome shape.

In another aspect of the inventive subject matter, one or more of the walls, and preferably the first wall, can additionally or alternatively comprise a plurality of protrusions configured to engage a portion of the lateral support. This engaging of the portion can advantageously maintain a vertical or horizontal position of the engaged portion of the lateral support with respect to the panel. It is further contemplated that the plurality of protrusions can engage a fastener disposed on the lateral support to thereby eliminate a need for a second fastener on the lateral support. For example, at least some of the plurality of protrusions could engage a hook or loop material of the lateral support to thereby secure a position of the lateral support with respect to the panel.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1 is a partial perspective view of one embodiment of a panel of the inventive subject matter.

FIG. 2 is a perspective view of one embodiment of protrusions composing a panel of the inventive subject matter.

FIG. 3 is a partial perspective view of one embodiment of a lateral support threaded through an aperture of one embodiment of a panel.

FIGS. 6A-C are partial perspective views of one embodiment of a brace of the inventive subject matter.

DETAILED DESCRIPTION

Figure 4:
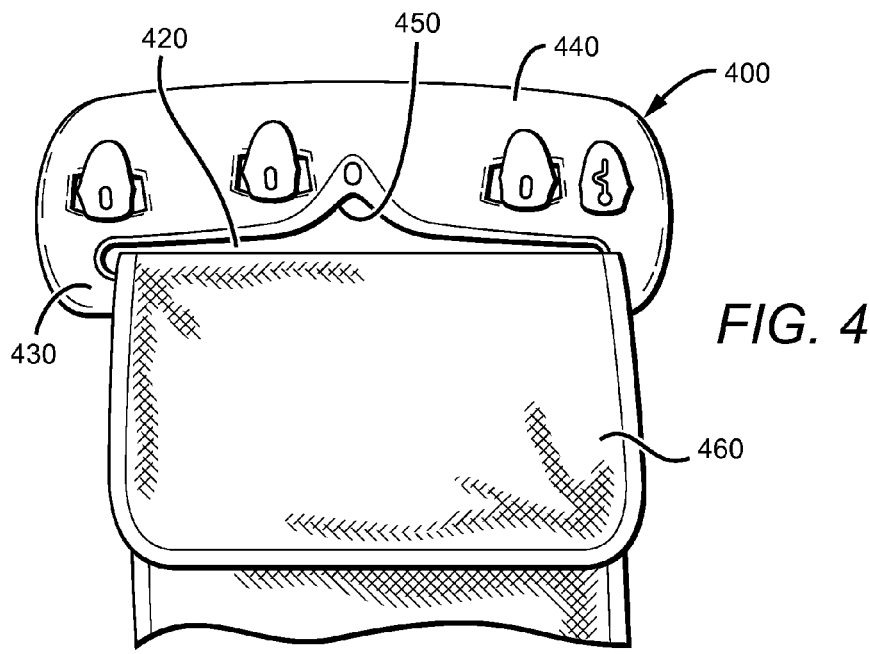
FIG. 4 is a partial view of one embodiment of a lateral support threaded through an aperture of one embodiment of a panel and fastened upon itself.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

FIG. 1 shows an embodiment of a panel of the inventive subject matter. Panel 100 advantageously can be coupled to at least one of a lateral support, a panel connector, a second panel, or any other suitable component of a brace.

Panel 100 preferably comprises a single integral piece of flexible material, and could be injection molded, for example. Panel 100 can comprise an inward curve configured to fit a lordotic curve of a wearer. Due to its flexible nature, the curve of panel 100 can be exaggerated, for example, by a tightening of the brace around a wearer. As used herein, the term "flexible" is used broadly to include materials that are capable of being slightly, moderately or substantially bent or curved without permanent deformation.

Alternatively, the panel of the inventive subject matter can be made from one or more pieces of material, and can be made of any suitable flexible or non-flexible material(s), including for example, a fabric, a padding, a soft plastic, or a rigid plastic.

Panel 100 comprises cord guides 160, retention device 170, which are described in further detail below. Panel 100 also comprises a first aperture 120, which is at least partially bordered by first portion 130 and second portion 140. It is contemplated that an aperture can be bordered by 1, 2, 3, 4, or even 5 or more portions or walls, depending on the configuration of the aperture.

Figure 9A:
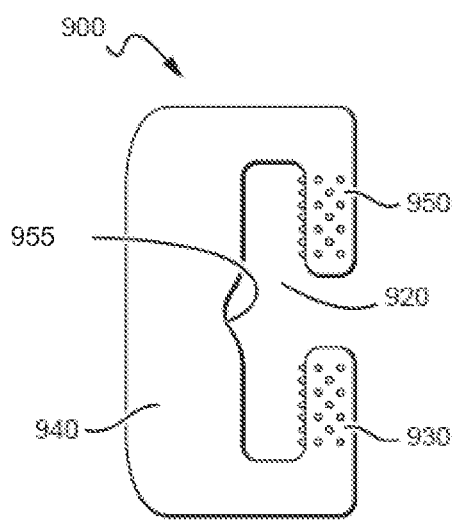
FIGS. 9A and 9B show two possible apertures of the inventive subject matter.

While aperture 120 comprises a through-hole, it is contemplated that an aperture of the inventive subject matter can comprise any suitable shape that is sized and dimensioned to at least partially accept an end portion of a lateral support. As examples, an aperture can comprise a substantially C-shape as shown in FIG. 9A, or a curved hole that does not run completely through the thickness of the panel (e.g. two openings on the same side of the panel that connect).

First portion 130 comprises a plurality of protrusions 110, which are configured to engage a portion of a lateral support (as shown in FIG. 3). The plurality of protrusions 110 advantageously help maintain a vertical position of the portion of the lateral support engaged by the protrusions, with respect to the first panel, when a portion of the lateral support is threaded through the aperture. This helps prevent the lateral support from collapsing or bunching up when worn by a wearer. Although it is contemplated that the plurality of protrusions could include a set of spikes, protrusions with rounded or flat ends are also contemplated.

Figure 11:
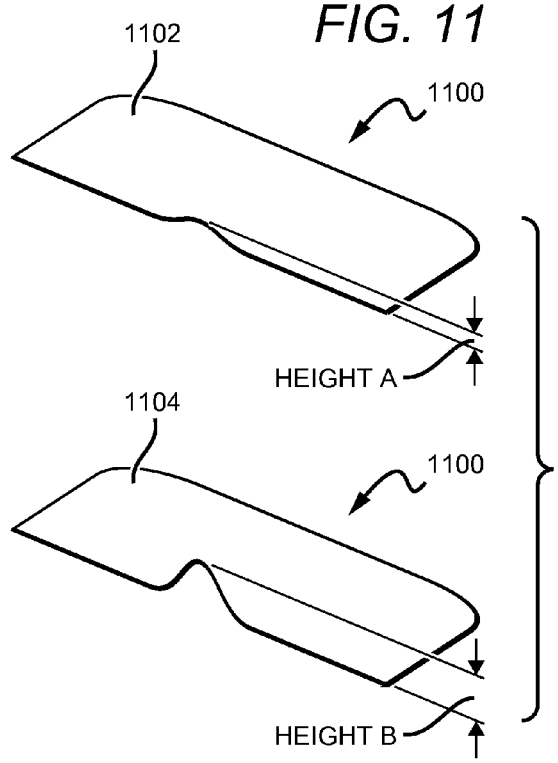
FIG. 11 is a schematic showing two portions of a panel having arcs of different dimensions.

Second portion 140 comprises an arced portion 150, which is configured to allow the first portion 130 or other portion of the panel to be pulled or otherwise manipulated without causing panel 100 to twist. While the embodiment shown in FIG. 1 only comprises a single arc, it is contemplated that a panel of the inventive subject matter can comprise any suitable number of arc (e.g., 2, 3, 4, etc.), each of the arcs can comprise the same or different shape (e.g., height, width, curvature, etc.). As shown in FIG. 11, a first portion 1102 of a panel 1100 partially defining an aperture can comprise an arc having a maximum height A (e.g., less than 3 mm, less than 2 mm, less than 1 mm, etc.), while a second portion 1104 of a panel 1100 partially defining the same aperture can comprise an arc having a larger maximum height B (e.g., 3 mm, 4 mm, 10 mm, 20 mm, or even larger, etc.). The arcs may be in the same or different directions. It is also contemplated that two or more arcs can be included on the same portion or wall of a panel.

Preferably, the arced portion comprises the inward curve configured to fit a lordotic curve of a wearer.

It is especially preferred that the first portion 130 comprises a substantially flat bottom surface while the second portion 140 comprises the arced portion 150. This advantageously allows the second portion 140 to flex inwardly toward a wearer when pressure is applied to the panel 100 such as via a lateral support or otherwise, while preventing the first portion 130 from flexing such that the first portion 130 can remain substantially flat. Without the arced portion 150, it is likely that the first portion 130 would flex outwardly to compensate for the inward flexing of the second portion 140 when at least a threshold pressure is applied to the panel 100.

Although shown having an arc 150, it is also contemplated that the entire second portion 140 could be arced.

FIG. 2 shows a close up view of a plurality of protrusions 210 on first portion 220 of panel 200. The plurality of protrusions are disposed on first surface 222 and second surface 224 of first portion 220, and first surface 222 at least partially defines a perimeter of aperture 230. In some other embodiments, it is contemplated that the plurality of protrusions can be disposed on 1, 3, 4, or even 5 or more surfaces of a portion/wall of a panel.

In this embodiment, each of the protrusions form an acute and obtuse angle with respect to the surfaces of the first portion because they extend out of the substantially flat surfaces at an angle. However, it is contemplated that one or more of the protrusions could form a right angle with respect to a flat surface. It is also contemplated that a surface of a portion/wall could comprise a non-flat surface (e.g., rounded, jagged, etc.) and that a protrusion could be disposed on the non-flat surface at any angle with respect to the surface.

A protrusion of the inventive subject matter can comprise any suitable shape, including for example, a mushroom shape having a rounded tip, an elongated sharp element, a serrated end, a substantially conical shape having a pointed tip, a folded over end (e.g., the loop portion of a hook and loop fastener, etc.), an hook shape with a pointed or rounded tip, or any other suitable shape. Moreover, a plurality of protrusions can all comprise protrusions having the same shape, or can comprise a combination of protrusions having different shapes.

Where a plurality of protrusions comprise at least some protrusions having a loop shape or a hook shape, or a hook or loop element is attached to (e.g., glued, welded, etc.) or molded into one or more of the walls, it is contemplated that the hooks or loops can couple with a hook or loop element of a lateral support, thereby providing a fastening mechanism between the panel and the lateral support, and eliminating the requirement of an additional fastener on the lateral support.

FIG. 3 shows a lateral support 360 having an end threaded through aperture 370 of first panel 300. As shown, first portion 330 of panel 300 comprises a plurality of protrusions 310, which are configured to couple with fabric of lateral support 360 and substantially maintain a position of the first lateral support 360 with respect to first panel 300.

FIG. 4 shows first lateral support 460 having one end threaded through aperture 420 of panel 400 and held substantially in place via a fastener (not shown) (e.g., hook and loop, button and aperture, a snap fastener comprising male and female portions, etc.). The two portions of fastener(s) can be on the same side of first lateral support 460, such that first lateral support 460 can thread through an aperture, fold over, and fasten upon itself. The arced portion 450 of second portion 440 allows a user to tug at first lateral support 460 (e.g., to tighten the brace, etc.) or cord, etc. coupled with panel 400 without substantially twisting or otherwise distorting panel 400.

Figure 5:
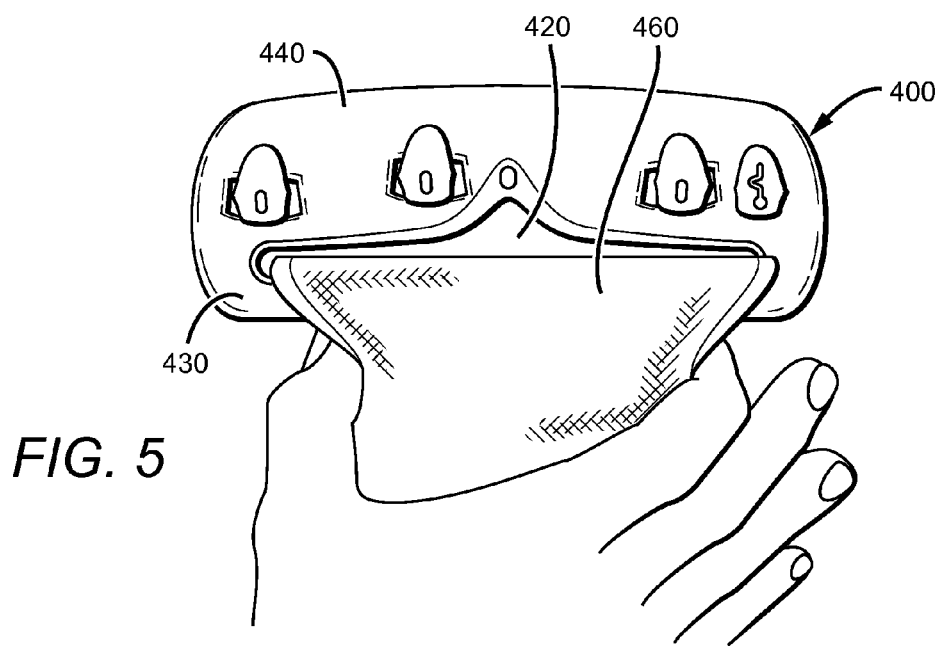
FIG. 5 is another partial view of the lateral support and panel from FIG. 6.

FIG. 5 shows the brace of FIG. 4, wherein a plurality of protrusions (not shown) have attached to the fold of lateral support 460, thereby preventing the fold from bunching up and causing discomfort to a wearer.

FIGS. 6A-C shows a brace of the inventive subject matter having a first panel 600 and a second panel 610 separate from the first panel 600, which are coupled together via first connector 640. Lumbar support 650 comprises a padding material, and is configured to couple with first connector 640 via fastener 645.

First panel 600 comprises a first aperture 601 at least partially defined by first portion 602 and second portion 603. First aperture 601 is sized and dimensioned to receive an end of first lateral support 620. As shown, a first side of support 620 comprises one or more fasteners that allows support 620 to fasten upon itself upon being thread through aperture 601.

In this particular embodiment, a first side of the end portion comprises a hook or loop material, and the remainder of the first side of the lateral support comprises a complementary material (hook or loop). Thus, the end portion can be coupled along various lengths of lateral support 620 depending on the size of the wearer, or the desired fit.

Second panel 610 comprises a second aperture 611 that is partially defined by a third portion 612 and fourth portion 613. Second aperture 611 is sized and dimensioned to receive an end portion of second lateral support 630. Similarly to first lateral support 620, second lateral support 630 comprises one or more fasteners that allows support 630 to fasten upon itself after being thread through aperture 611 and folded over.

Figure 7:
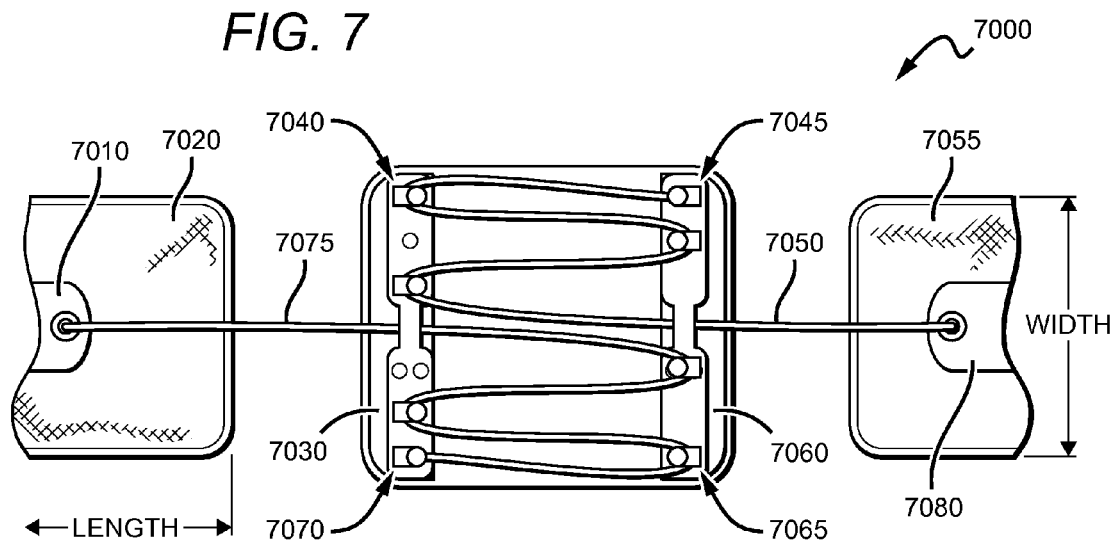
FIG. 7 is a top view of a cord system of the inventive subject matter.

FIG. 7 shows an embodiment of a brace of the inventive subject matter having first and second sets of cord guides. Brace 7000 comprises first panel 7030 and second panel 7060, which are coupled together via a connector that attaches to both panels. It is contemplated that the connector can attach to one or more panels via any suitable attachment means, including for example, gluing, welding, stitching, or stapling.

First panel 7030 comprises or is coupled to a first set of cord guides 7040 comprising one or more cord guides, and a third set of cord guides 7070 comprising one or more cord guides. Second panel 7060 comprises or is coupled to a second set of cord guides 7045 comprising one or more cord guides, and a fourth set of cord guides 7065 comprising one or more cord guides.

Each cord guide can comprise a rotating or non-rotating cord guide, and is sized and dimensioned to receive at least one of a first cord 7050 and a second cord 7075. First cord 7050 is sequentially thread back and forth across a portion of the connector, from a cord guide of the first set of cord guides 7030 to a cord guide of the second set of cord guides 7045, such that pulling on the first cord 7050 in a first direction shortens a distance between a top portion of first panel 7030 and a top portion of second panel 7060. Second cord 7075 is sequentially thread back and forth across a portion of the connector, from a cord guide of the third set of cord guides 7070 to a cord guide of the fourth set of cord guides 7065, such that pulling on the second cord 7075 in a second direction shortens a distance between a bottom portion of the first panel 7030 and a bottom portion of the second panel 7060.

In some embodiments, a brace can comprise a single cord threaded through a first and second set of cord guides, such that when the first cord is pulled in a first direction, a distance between the first panel and the second panel can be shortened.

Figure 8A:
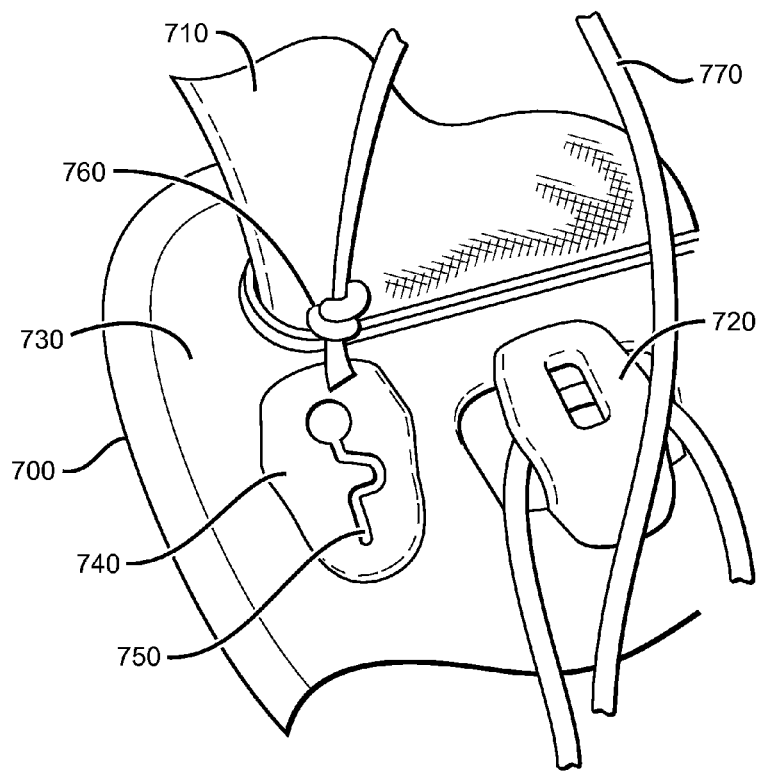
FIGS. 8A and 8B are partial views of a cord guide and retention device of the inventive subject matter.
Figure 8B:
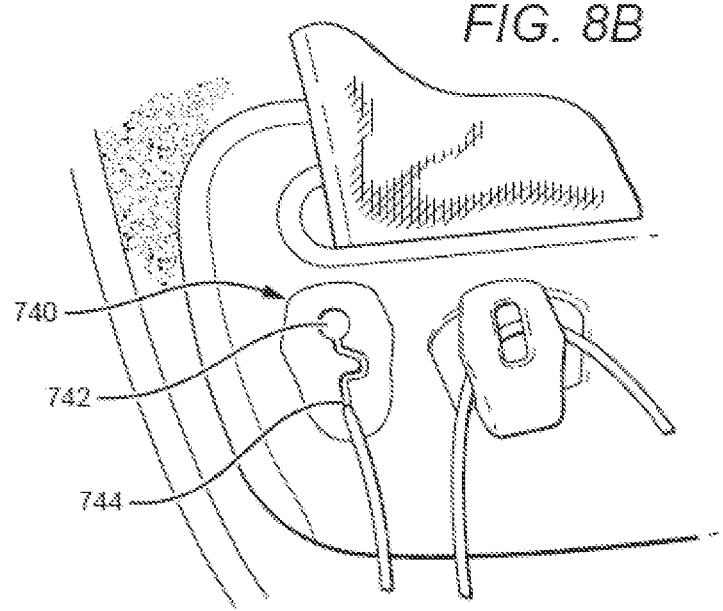

Brace 7000 further comprises a first pull tab 7080 and second pull tab 7010. First pull tab 7080 is coupled with first cord 7050, and comprises a fastener that is configured to interact with a fastener of the lateral second support 7055 and secure the first pull tab 7080 to second lateral support 7055. It is contemplated that second lateral support 7055 can comprise one or more fasteners along a substantial length of a first side of support 7055 (e.g., a large strip of hook or loop fastener, etc.), such that the fastener of pull tab 7080 (e.g., hook or loop fastener, etc.) can interact with (e.g., couple with, attach to, etc.) a fastener of the lateral support 7055 along various portions of its length or width. Second pull tab 7010 is coupled with second cord 7075, and comprises a fastener that is configured to interact with a fastener of first lateral support 7020, FIGS. 8A-B show a portion of a panel of the inventive subject matter having a cord guide and a cord retention device. First panel 700 comprises a first portion 710 and second portion 730. The first portion 710 comprises a plurality of protrusions (not shown), which are configured to substantially block a movement of a lateral support. The second portion 730 comprises a first cord guide 720, sized and dimensioned to receive cord 770, and a cord retention device 740, configured to stop cord 770 from retracting beyond a specified point (e.g., where cord block 760 is).

As used herein, the term "cord block" is used very broadly, and can include a knot, multiple knots, a piece of wood, metal, plastic or other material that surrounds a portion of a cord, or any other item that has a diameter or width that is larger than the diameter or width of the cord itself.

As shown, cord retention device 740 comprises an aperture having a first end 742 and second end 744. The first end 742 comprises a first width, and is sized and dimensioned to readily receive cord 770 and cord block 760. The second end 744 comprises a second width smaller than the first width, and is sized and dimensioned to readily receive cord 770, but not cord block 760, which has a smaller width or diameter than cord 770. It is contemplated that the first width can be larger than, equal to, or even smaller than a diameter or width of cord block 760. Where the first width is smaller than a diameter or width of cord block 760, the cord block 760 can still be readily received by first end where cord block 760 is compressible. Similarly, second width can be larger than, equal to, or even smaller than a diameter or width of cord 770. Where the second width is smaller than a diameter or width of cord 770, the cord 770 can still be readily received by second end where cord 770 is compressible. It is contemplated that the first width can be determined as a function of a diameter or width of a cord block, and that the second width can be determined as a function of a diameter or width of a cord.

Figure 9B:
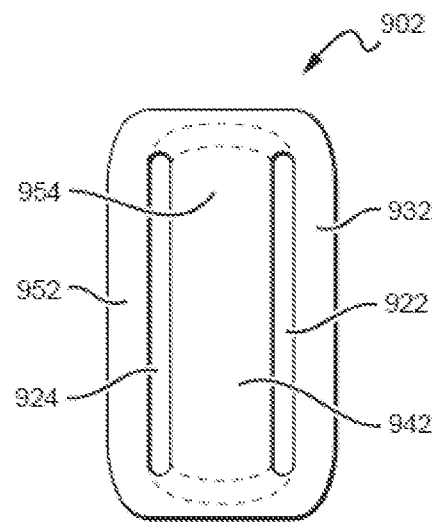

FIGS. 9A-9B illustrate different embodiments of a panel of the inventive subject matter. FIG. 9A illustrates a panel 900 having a "c-shape", which includes an aperture 920 at least partially defined by first, second, and third portions 930, 940, and 950, respectively, of the panel 900. The second portion 940 can include an arced portion 955 that includes an inward curve configured to fit a lordotic curve of a wearer.

FIG. 9B illustrates a panel 902 having first and second apertures 922 and 924. The first aperture 922 can be at least partially defined by first and second portions 932 and 942, while the second aperture 924 can be at least partially defined by the second portion 942 and a third portion 952. Preferably, the second portion 942 includes an arced portion 954 illustrated by the dotted lines.

Figure 10:
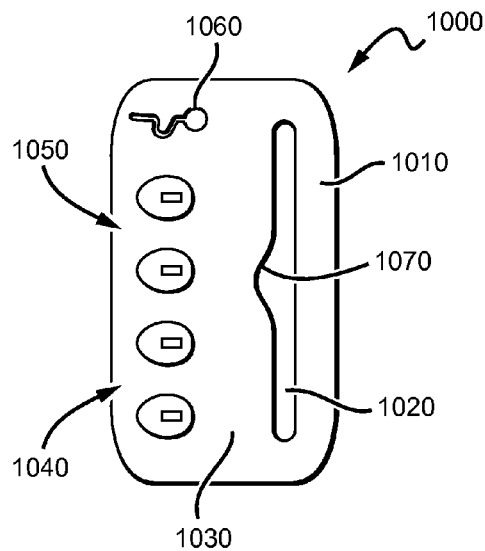
FIG. 10 is a schematic of one embodiment of a panel of the inventive subject matter comprising a slit instead of an aperture.

FIG. 10 shows a possible embodiment of a panel of the inventive subject matter. Panel 1000 comprises a first portion 1010 and second portion 1030 that define a slit 1020. Second portion 1030 comprises a first and second set of cord guides, 1050 and 1040, respectively, a retention device 1060, and an arc 1070. It is contemplated that a lateral support or other element can couple with panel 1000 via a hook and loop fastener, buttons, snaps, magnets, sewing, welding, gluing, or any other commercially suitable means. For example, an end portion of a lateral support can be stitched to an edge of first portion 1010.

Figure 12:
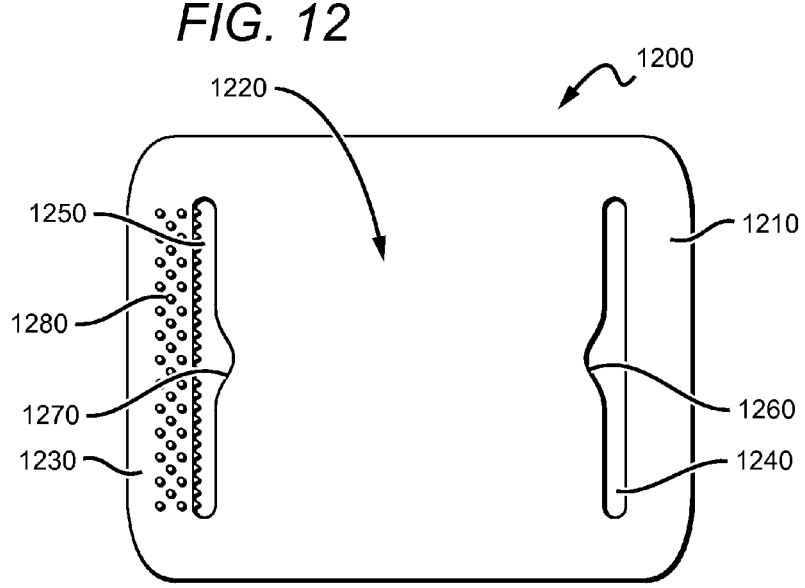
FIG. 12 is a schematic of an embodiment of a panel of the inventive subject matter having two apertures.

FIG. 12 shows an embodiment of a panel of the inventive subject matter having two apertures. First panel 1200 comprises a first aperture 1240 that is at least partially defined by first portion 1210 and second portion 1220. First panel 1200 also comprises a second aperture that is at least partially defined by second portion 1220 and third portion 1230. First aperture 1240 can be sized and dimensioned to receive an end of a first lateral support, and second aperture 1250 can be sized and dimensioned to receive an end of a second lateral support, or the first lateral support upon being wrapped around a waist of a wearer.

The second portion 1220 comprises a first arc 1260 and a second arc 1270, which advantageously prevent panel 1200 from twisting when a lateral support or cord, etc. is pulled in a first direction by a user. Where a brace of the inventive subject matter comprises a single lateral support, it is contemplated that a first end of the lateral support can be threaded through first aperture 1240 and fastened upon itself, and a second end of the lateral support can be threaded through second aperture 1250 and fastened upon itself. Where a brace of the inventive subject matter comprises two lateral supports, it is contemplated that a first end of the first lateral support can be threaded through first aperture 1240, while a first end of the second lateral support can be threaded through second aperture 1240. The second end of the first lateral support can then be wrapped over a second end of the second lateral support and couple together via a fastener. For example, each of the first and second lateral supports can comprise a hook material on a front side and a loop material on the back side. When the second end of the first lateral support is wrapped over a second end of the second lateral support, the loop material on the back side of the second end of the first lateral support can couple with the hook material on the front side of the second end of the second lateral support and secure the brace to the wearer.

If the brace described above also comprises a cord system, a pull tab of the cord system can comprise a loop material that is configured to couple with the hook material on the front side of the first or second lateral supports.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A brace configured to provide support to a lower spine of a wearer, comprising:
   a first panel having first and second portions, wherein the first and second portions at least partially define a first aperture;
   a first lateral support having a first fastener;
   a second panel coupled to the first panel and having third and fourth portions, wherein the third and fourth portions at least partially define a second aperture;
   a second lateral support;
   wherein a first end of the first lateral support is sized and dimensioned to thread through the first aperture;
   wherein the second portion of the first panel is arced;
   wherein a first end of the second lateral support is sized and dimensioned to thread through the second aperture; and
   wherein a second end of the second lateral support is configured to be secured to a second end of the first lateral support to secure the brace to the wearer.

2. The brace of claim 1, wherein a distance between a minimum and a maximum height of the arch of the second portion is at least three millimeters.

3. The brace of claim 1, wherein the first panel comprises a single integral piece that includes the first and second portions.

4. The brace of claim 3, wherein the single integral piece is composed of a flexible material.

5. The brace of claim 1, wherein the first panel comprises an inward curve configured to fit a lordotic curve of the wearer.

6. The brace of claim 5, wherein the arced second portion comprises the inward curve.

7. The brace of claim 1, wherein the first portion has a bottom surface that is substantially flat.

8. The brace of claim 1, further comprising:
 a first set of cord guides coupled to the first panel, each of the cord guides of the first set configured to receive a first cord;
 a second set of cord guides coupled to the second panel, each of the cord guides of the second set configured to receive the first cord; and
 wherein the first cord is sequentially thread back and forth across a sagittal plane of the wearer from a cord guide of the first set to a cord guide of the second set, such that pulling on the first cord in a first direction shortens a distance between the first panel and the second panel.

9. A brace configured to provide support to a lower spine of a wearer, comprising:
 a first panel having first and second portions, wherein the first and second portions at least partially define a first aperture;
 a first lateral support having a first fastener;
 wherein a first end of the first lateral support is sized and dimensioned to thread through the first aperture, and wherein the second portion of the first panel is arced;
 a first set of cord guides coupled to the first panel, each of the cord guides of the first set configured to receive a first cord;
 wherein the first cord includes a pull tab; and
 a cord retention device coupled to the first panel, wherein the cord retention device includes a second aperture having a first end and a second end, where the first end comprises a first width and is sized and dimensioned to allow receipt of a cord block of the first cord, and where the second end comprises a second width smaller than the first width to prevent the cord block from passing through the second end.

10. The brace of claim 9, wherein the first width is at least twice as large as the second width.

11. The brace of claim 9, wherein the first panel comprises a single integral piece that includes the first and second portions, the first set of cord guides, and the cord retention device.

12. The brace of claim 9, further comprising:
 a second panel having third and fourth portions, wherein the third and fourth portions at least partially define a second aperture;
 wherein a second end of the first lateral support is sized and dimensioned to thread through the second aperture.

13. A brace configured to provide support to a lower spine of a wearer, comprising:
 a first panel having first and second portions, wherein the first and second portions at least partially define a first aperture;
 a first lateral support having a first fastener;
 wherein a first end of the first lateral support is sized and dimensioned to thread through the first aperture, and wherein an edge of the second portion that at least in part defines the first aperture is arced and configured to flex inwardly towards the wearer when the brace is worn; and
 wherein the first panel comprises a third portion, and wherein the second portion is disposed between the first and third portions, and wherein the second and third portions at least partially define a second aperture configured to receive at least one of (a) a second end of the first lateral support and (b) a first end of a second lateral support.

14. A brace configured to provide support to a wearer, comprising:
 a first panel having first and second portions and including a first aperture, wherein the first aperture is bordered by first and second portions of the first panel;
 a first lateral support having a first end that is sized and dimensioned to thread through the first aperture;
 wherein the first portion comprises a plurality of protrusions configured to (a) engage a portion of the first lateral support and (b) maintain a position of the portion of the first lateral support with respect to the first panel, when the first end of the first lateral support is threaded through the first aperture; and
 wherein the first panel comprises a single integral piece that includes the first and second portions, the plurality of protrusions, and a first set of cord guides.

15. The brace of claim 14, wherein the plurality of protrusions are disposed on first and second surfaces of the first portion.

16. The brace of claim 14, wherein a side of at least one of the protrusions forms an acute angle with respect to a first surface of the first portion.

17. The brace of claim 14, wherein at least one of the plurality of protrusions includes a pointed tip.

18. The brace of claim 14, wherein at least one of the plurality of protrusions includes a rounded tip.

19. The brace of claim 14, wherein at least one of the first and second portions of the first panel is arced.

* * * * *